(12) United States Patent
Debray

(10) Patent No.: US 9,893,423 B2
(45) Date of Patent: Feb. 13, 2018

(54) ELECTROMAGNETIC WAVE SENSOR AND/OR EMITTER

(71) Applicant: CANON KABUSHIKI KAISHA, Tokyo (JP)

(72) Inventor: Alexis Debray, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 140 days.

(21) Appl. No.: 14/534,030

(22) Filed: Nov. 5, 2014

(65) Prior Publication Data

US 2015/0130481 A1    May 14, 2015

(30) Foreign Application Priority Data

Nov. 13, 2013  (JP) .................................. 2013-235033

(51) Int. Cl.

| | |
|---|---|
| *H01Q 7/00* | (2006.01) |
| *G01N 22/00* | (2006.01) |
| *G01R 27/06* | (2006.01) |
| *G01R 27/00* | (2006.01) |
| *H01Q 1/24* | (2006.01) |
| *H01Q 5/40* | (2015.01) |
| *G01S 13/89* | (2006.01) |
| *G01S 13/02* | (2006.01) |

(52) U.S. Cl.
CPC .............. *H01Q 7/00* (2013.01); *G01N 22/00* (2013.01); *G01R 27/00* (2013.01); *G01R 27/06* (2013.01); *H01Q 1/248* (2013.01); *H01Q 5/40* (2015.01); *G01S 13/0209* (2013.01); *G01S 13/89* (2013.01)

(58) Field of Classification Search
CPC ........ G01N 22/00; G01R 27/00; G01R 27/06; H01Q 1/248; H01Q 7/00; H01Q 5/335; H01Q 5/40; H01Q 5/50; G01S 13/0209; G01S 13/89
USPC ........ 324/600, 629, 637; 343/728, 732, 741, 343/748, 764, 788, 842, 853, 855, 866
See application file for complete search history.

(56) References Cited

U.S. PATENT DOCUMENTS

| | | | |
|---|---|---|---|
| 6,057,803 A | 5/2000 | Kane et al. | |
| 6,225,955 B1 * | 5/2001 | Chang | .................... H01Q 19/13 343/720 |
| 7,512,511 B1 * | 3/2009 | Schultz | ............... F41H 13/0068 250/250 |

(Continued)

FOREIGN PATENT DOCUMENTS

| | | |
|---|---|---|
| JP | H09-260925 A | 10/1997 |
| JP | 2001-292019 A | 10/2001 |

(Continued)

*Primary Examiner* — Hoai-An D Nguyen
(74) *Attorney, Agent, or Firm* — Fitzpatrick, Cella, Harper & Scinto

(57) ABSTRACT

Provided is a device for performing at least one of detection and emission of electromagnetic waves, including a plurality of antennas, in which a first antenna includes a first radiating element and a first electronic element electrically connected to the first radiating element, and is sensitive to a first frequency band, and in which a second antenna includes a second radiating element and a second electronic element electrically connected to the second radiating element, and is sensitive to a second frequency band. At least a part of the second radiating element is arranged inside the first radiating element.

19 Claims, 16 Drawing Sheets

(56) References Cited

U.S. PATENT DOCUMENTS

| | | | |
|---|---|---|---|
| 7,783,271 B2* | 8/2010 | Samuels | H03D 7/163 |
| | | | 455/105 |
| 8,344,950 B2 | 1/2013 | Su | |
| 9,548,039 B2* | 1/2017 | Arasawa | G09G 3/20 |
| 2001/0010507 A1* | 8/2001 | Hiroshima | H01P 1/2056 |
| | | | 343/853 |
| 2004/0214530 A1* | 10/2004 | Brandt | H04B 1/48 |
| | | | 455/90.1 |
| 2007/0279231 A1* | 12/2007 | Cheng | G06K 19/07786 |
| | | | 340/572.7 |
| 2008/0062066 A1* | 3/2008 | Arai | H01Q 1/2208 |
| | | | 343/867 |
| 2008/0191959 A1* | 8/2008 | Koyama | H01Q 1/2283 |
| | | | 343/873 |
| 2008/0210762 A1* | 9/2008 | Osada | G06K 19/0701 |
| | | | 235/492 |
| 2009/0280743 A1 | 11/2009 | Gast et al. | |
| 2011/0156721 A1* | 6/2011 | Icove | G01K 11/006 |
| | | | 324/629 |
| 2013/0009836 A1* | 1/2013 | Islam | H01Q 21/30 |
| | | | 343/810 |
| 2013/0018440 A1* | 1/2013 | Chow | A61N 1/3787 |
| | | | 607/61 |
| 2013/0261703 A1* | 10/2013 | Chow | A61N 1/3605 |
| | | | 607/61 |
| 2014/0008992 A1* | 1/2014 | Leabman | H01F 38/14 |
| | | | 307/104 |
| 2014/0326890 A1 | 11/2014 | Debray et al. | |
| 2015/0034825 A1 | 2/2015 | Debray et al. | |
| 2015/0077299 A1* | 3/2015 | Tatarnikov | H01Q 5/328 |
| | | | 343/749 |
| 2015/0326070 A1* | 11/2015 | Petras | H02J 7/025 |
| | | | 307/104 |
| 2016/0127972 A1* | 5/2016 | Ananthanarayanan | H04W 36/30 |
| | | | 370/332 |

FOREIGN PATENT DOCUMENTS

| | | |
|---|---|---|
| JP | 2005-341313 A | 12/2005 |
| JP | 2007-180762 A | 7/2007 |
| JP | 2009-273129 A | 11/2009 |
| JP | 2010-219652 A | 9/2010 |
| JP | 2013-214939 A | 10/2013 |
| JP | 2015-043526 A | 3/2015 |

* cited by examiner 12B-12B CROSS SECTION 14B-14B CROSS SECTION

_US 9,893,423 B2_

ELECTROMAGNETIC WAVE SENSOR AND/OR EMITTER

BACKGROUND OF THE INVENTION

Field of the Invention

The present invention relates to a device for performing at least one of detection and emission of electromagnetic waves, and more particularly, to an electromagnetic wave sensor or emitter operating with an electromagnetic wave having an arbitrary frequency band in the frequency range from millimeter waves to terahertz (THz) (30 GHz to 30 THz) (hereinafter also referred to as "terahertz wave"). In the following, the electromagnetic wave sensor and/or emitter is represented by a sensor in some cases.

Description of the Related Art

When terahertz waves are used, imaging of a test object can be realized at a resolution of 1 millimeter or less. In addition, many molecules are sensitive to a specific frequency component in the terahertz range, and hence terahertz waves can be used for the spectroscopic analysis of materials. With this feature of terahertz waves, it is possible to build a system operating in the terahertz range that carries out both imaging and spectroscopic analysis of a test object. For example, an image showing what kind of compound is present at what position of the test object can be formed. Many applications are expected from this feature in the medical field, security field, and manufacturing field.

U.S. Pat. No. 8,344,950 reports on a module comprising a dual-loop and multi-frequency antenna. This module includes a radiating element in which two loops are electrically connected to the same shorting unit and to the same feeding unit, the smaller of the two loops being included into the larger one. The two loops are therefore electrically connected together. This design allows for the simultaneous usage of two frequency bands (2.4 GHz and 5 GHz) for a wireless LAN (local area network) access-point. Thanks to this design using a dual-loop, the antenna of the system can be made smaller than previous dual band antennas and therefore more appealing aesthetically. In order to have a high efficiency, the radiation impedance of the dual-loop antenna and the impedance of the feeding unit must be matched to each other (conjugate matching).

SUMMARY OF THE INVENTION

Terahertz waves can be applied to an image sensor in the same manner as microwaves technology. Moreover terahertz waves can be also used for spectroscopy. By combining these two features, the imaging of molecule composition can be achieved. To achieve the imaging of molecule composition, it is required that a terahertz-wave image sensor measures several frequencies at each position of the image. In optical photography, in order to record several colors, pixels which have sensitivities to red, green, and blue, need to be arranged adjacent to one another in a focal plane array (FPA). In a similar manner, pixels which are sensitive to different frequencies need to be arranged. As a result, the FPA in this case becomes larger in size than an FPA which is sensitive to only one frequency. This fact is a problem especially in the terahertz range. For example, the wavelength $\lambda$ corresponding to 1 THz in vacuum is 300 μm, and the size of the surface area of each pixel is roughly of the order of $\lambda^2$. Therefore, the size of the FPA including a million of pixels which is sensitive to four frequencies is 60 cm×60 cm. An FPA having this size cannot be manufactured by using today's very large scale integrated (VLSI) technology because it is limited to a wafer standard size of 12 inches.

Although in the microwave range it is possible to produce a matching circuit in order to match the impedance of the antenna and that of the feeding unit, this is not straightforward in the terahertz range because inductors and capacitors are not well developed yet in the terahertz range. Therefore, the antenna and the feeding unit must be designed in order for their respective impedance to match directly, i.e. without a matching circuit. When considering two antennas connected together and to a single feeding unit, it is unlikely, in general, that impedance matching condition will be preserved for the resulting antenna because the current distribution in the radiating element will be perturbed and so will be its radiation impedance. As a result, it is difficult for the system of two antennas connected together to have a high efficiency due to the impedance mismatching between the radiating element and the feeding portion. Because of this, the system described above is difficult to be used in the terahertz range. In other words, the antenna described above has sensitivity to the two frequency bands. However, there is no proposal of a technology about a control method for the radiation impedance of the antenna. As a result, in the terahertz range, the impedance matching between the radiating element and the feeding portion is not sufficiently achieved, and the efficiency of the system is thus low.

In view of the foregoing, it is therefore an object of the present invention to provide an electromagnetic wave sensor or emitter having relatively small size and in which the impedance of the receiving/radiating element directly matches the impedance of the electronic element (without using a matching circuit or the like) in a plurality of frequency bands. For this purpose a device is proposed where a plurality of antennas each including a radiating element and a feeding unit have sensitivities to a plurality of different frequency bands, and the impedance matching in the terahertz range is separately achieved between the radiating elements and the feeding units.

According to one embodiment of the present invention, a device sensing electromagnetic waves which consists of at least two antennas is provided:

the first antenna including:

a first radiating element, a first electronic element electrically connected to the first radiating elements;

the first antenna being sensitive to a first frequency band of interest, the second antenna including:

a second radiating element partially placed inside the first radiating element, a second electric element electrically connected to the second radiating elements;

the second antenna being sensitive to a second frequency band of interest.

According to another embodiment of the present invention, an apparatus is provided which includes a plurality of the devices sensing electromagnetic waves according to claim 1 including a first and second devices sensing electromagnetic waves, wherein, in the first devices sensing electromagnetic waves, an antenna that is sensitive to a higher frequency is sensitive to first polarization and an antenna that is sensitive to a lower frequency is sensitive to second polarization, and wherein, in the second device sensing electromagnetic waves, an antenna that is sensitive to the lower frequency is sensitive to the first polarization, and an antenna that is sensitive to the higher frequency is sensitive to the second polarization.

Note that, in this specification, "radiating" and "reception/radiation" mean at least one of the electromagnetic wave reception or the electromagnetic wave radiation.

Further features of the present invention will become apparent from the following description of exemplary embodiments with reference to the attached drawings.

DESCRIPTION OF THE EMBODIMENTS

Figure 1A:
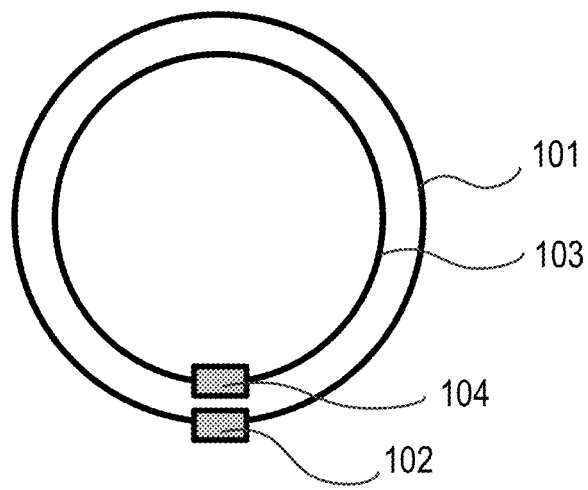
FIG. 1A shows a top view of a first variation of the first embodiment.

In a device sensing electromagnetic waves according to one embodiment of the present invention, one radiating element surrounds in its inside at least a part of another radiating element. When the shape of the larger of the electromagnetic wave sensors has a closed form such as a closed curved line, the meaning of "inside" is clear. In this case, when the second radiating element is entirely present in the inside of the first radiating element, the second radiating element does not cross the first radiating element. On the other hand, when the shape of the larger of the electromagnetic wave sensors has an opened form, an area surrounded by a line connecting both the opened ends and the opened radiating element is present in the inside. The surface area of a sensor structured in such a manner can be reduced to be smaller than that of a sensor in which a plurality of antennas are arranged adjacent to one another. In addition, the impedance of a radiating element can be directly matched with the impedance of a corresponding electronic element which is electrically connected to the radiating element in a predetermined frequency band, and hence the efficiency of the antenna can be increased. Moreover, one radiating element surrounds in its inside at least a part of the other radiating element, and hence the size can be reduced. This advantage becomes important when the present invention is applied to an image sensor (especially, an image sensor corresponding to a terahertz range). In other words, an image sensor having a minimum size that does not deteriorate performance thereof can be realized. An electromagnetic wave treated in this electromagnetic wave sensor and emitter contains a component of a frequency of, for example, from 0.1 terahertz to 10 terahertz.

(First Embodiment)

A first embodiment of the present invention is described as follows. A first rectifier is electrically connected to a first radiating element extending curved-linearly or bent curved-linearly. In a given frequency band, complex impedances of the radiating element and of the rectifier are conjugately matched. Therefore, in this frequency band of the first antenna, the efficiency of this sensing system is maximum. Several rectifying elements can be envisioned for this antenna. For example, Schottky barrier diodes have been investigated in the THz range and can operate at room temperature. More recently, a rectifier (plasmon rectifier) in the THz range and operating at room temperature have been demonstrated using plasmons in the electronic gas of field effect transistors.

A second rectifier is electrically connected to a second radiating element similarly extending linearly. Similarly to the case of the first antenna, there is a frequency band in which the impedances of the two elements are conjugatively matched, and the sensitivity becomes maximum. In order to reduce the physical footprint of the sensor formed by the two antennas, the second radiating element is designed with a surface area with is smaller than that of the first radiating element and is placed inside the first radiating element. If the two radiating elements are planar and placed in the same plane, as described above, the notion of "inside" is easily understood. Even if the two radiating elements are not placed in the same plane but in two parallel planes, respectively, it is preferred that the two radiating elements be placed at a distance of $\lambda/10$ or less ($\lambda$ is the longest wavelength of the related wavelength band). The same may be true even when the two radiating elements are not planar.

Figure 1B:
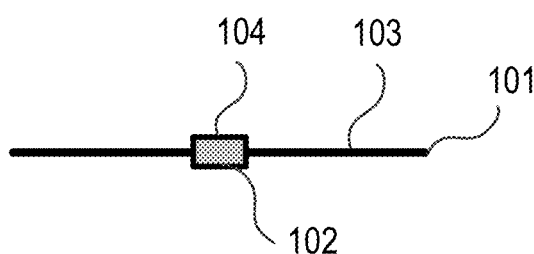
FIG. 1B shows a side view of a first variation of the first embodiment.

FIG. 1A and FIG. 1B show a first variation of the first embodiment in which the first radiating element 101 is a circular loop with a given diameter. This circular loop is electrically connected to a first rectifying element 102. A second radiating element 103 is also a circular loop which diameter is smaller than that of the first loop. This second circular loop is electrically connected to a second rectifying element 104. As a result, the surface area of the second loop with the smaller diameter is smaller than that of the first loop and the entire second loop can be placed inside the first loop as illustrated in FIG. 1A. In this first variation, the electrical wires constituting the second loop radiating element does not cross the first loop radiating element, and hence the second wiring loop does not extend to the outside of the first wiring loop. This configuration is more preferred in the following point than a different configuration. In the different configuration, in general, a radiation impedance of the first radiating element 101 does not sufficiently match with an impedance of the first rectifier 102 because a given frequency band changes, resulting in a poor efficiency of the first sensor in some cases.

Figure 1C:
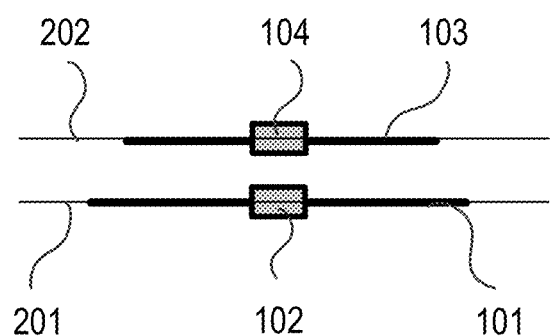
FIG. 1C shows a side view of a first variation of the first embodiment.

FIG. 1C is a side view of another variation of the first embodiment. In this case, the first antenna and the second antenna are not placed in the same plane but in two parallel planes 201 and 202. In this case, it is preferred that the two planes are not a distance of $\lambda/10$ or less.

Figure 2A:
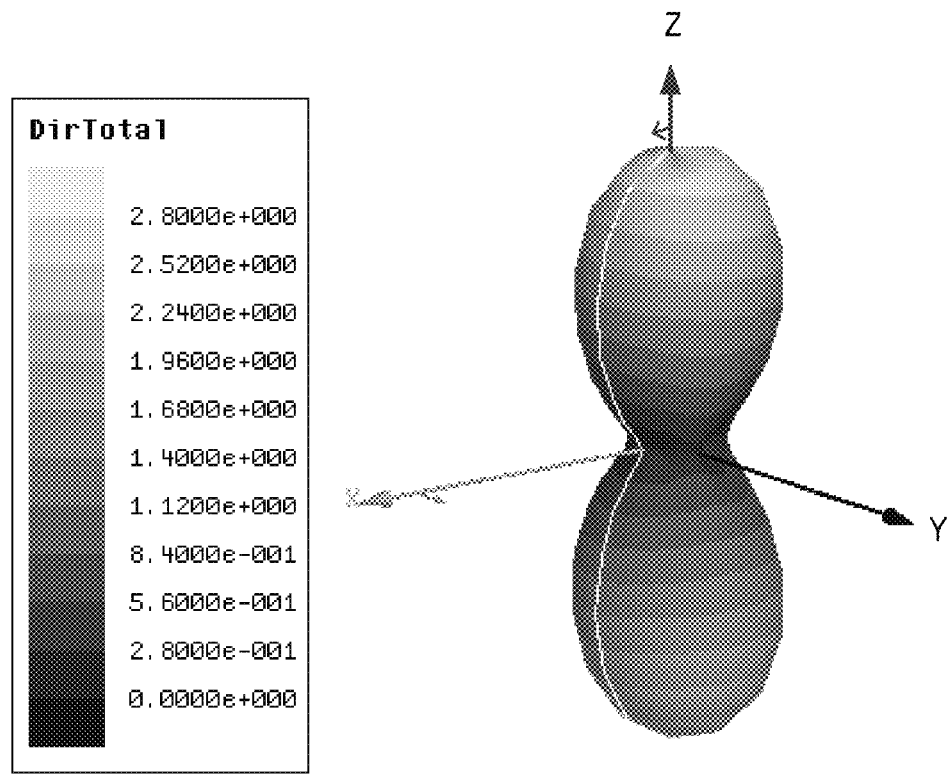
FIG. 2A shows a view illustrating a radiation pattern (directivity) of a loop antenna around a second antiresonant frequency.
Figure 2B:
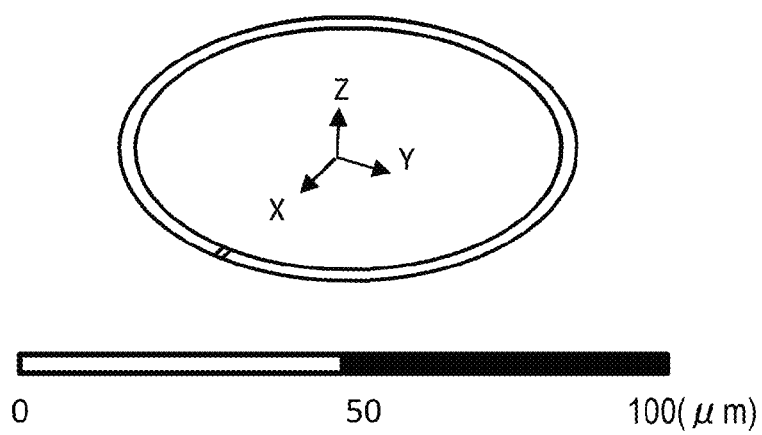
FIG. 2B shows a view illustrating the loop antenna around the second antiresonant frequency.

In this embodiment, this invention is particularly interesting if the radiating loop is excited around a second antiresonant frequency. FIG. 2A shows a radiation pattern (directivity) of a circular loop antenna measured around the second antiresonant frequency. A commercially available finite element software HFSS (manufactured by Ansoft Corporation) was used. An antenna having a configuration illustrated in FIG. 2B was used for the simulations. The radius of the loop is 75 μm and the width is 4 μm. The loop is placed in vacuum in a plane XY. As can be seen from the simulations, the directivity in the direction perpendicular to the plane is 10 times or more than that in the direction within the plane. As a result, the sensitivity of the antenna in the direction perpendicular to the plane is 10 times or more than that in the direction within the plane. Therefore, the sensitivity of the antenna to the electromagnetic wave in the direction within the plane is much smaller than the sensitivity to the electromagnetic wave in the direction perpendicular to the plane.

Moreover, because the loop antenna of the second antenna is excited at the second antiresonant frequency, the influence of the first antenna on the second antenna is very small. The reason for this is because the intensity of an electromagnetic field reemitted (scattered) by the second loop antenna will be 10 times smaller than the original impinging electromagnetic field. Although the radiation pattern gives the direction of the radiation in the far-field, and not the electro-magnetic field near the antenna where the second antenna is placed, the radiation pattern is nevertheless used as a first approximation in order to understand the influence of the antennas on each others.

Figure 3A:
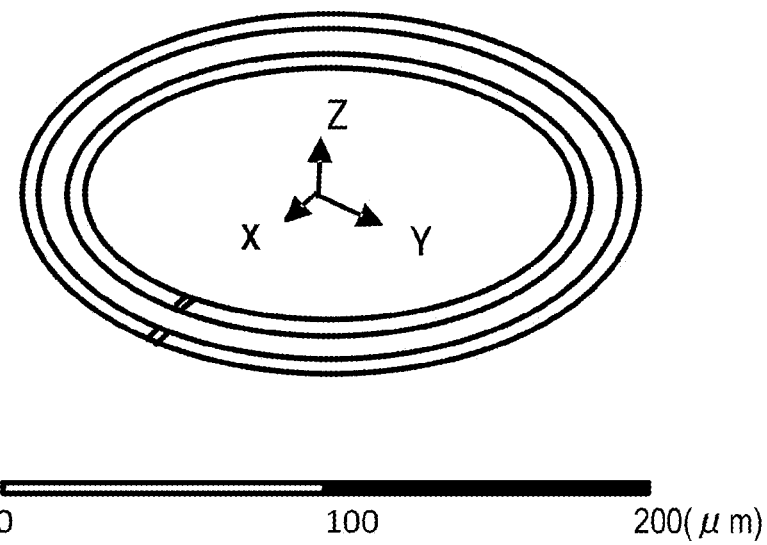
FIG. 3A shows a view illustrating a loop antenna used for calculation of FIG. 4B.
Figure 3B:
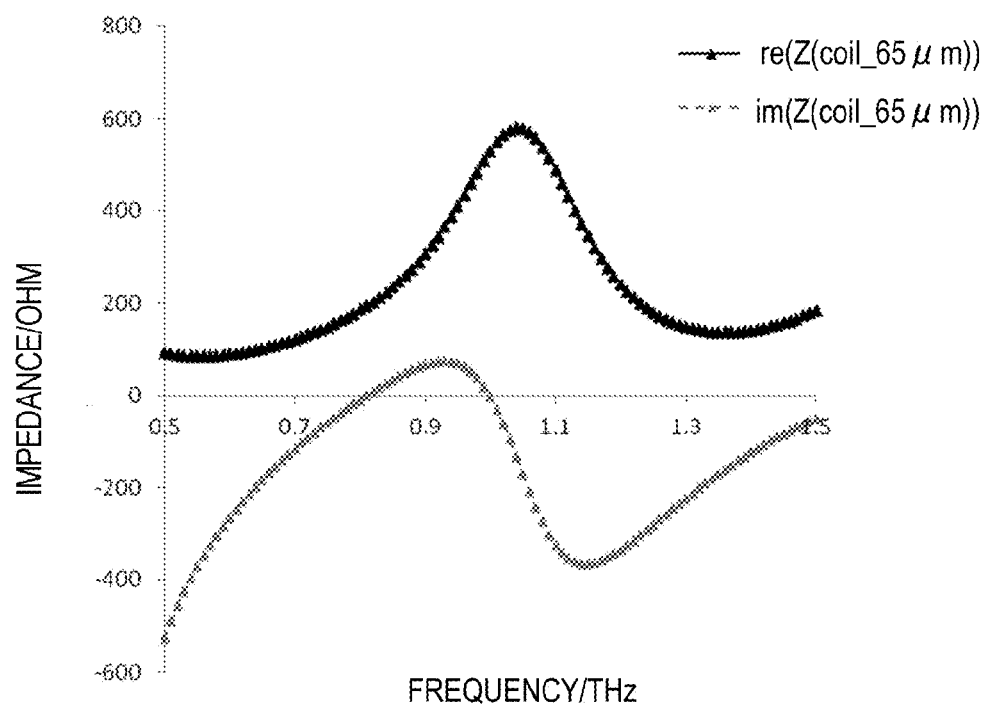
FIG. 3B shows a graph showing an impedance of the loop antenna, 65 μm in radius, around its second antiresonant frequency.
Figure 4A:
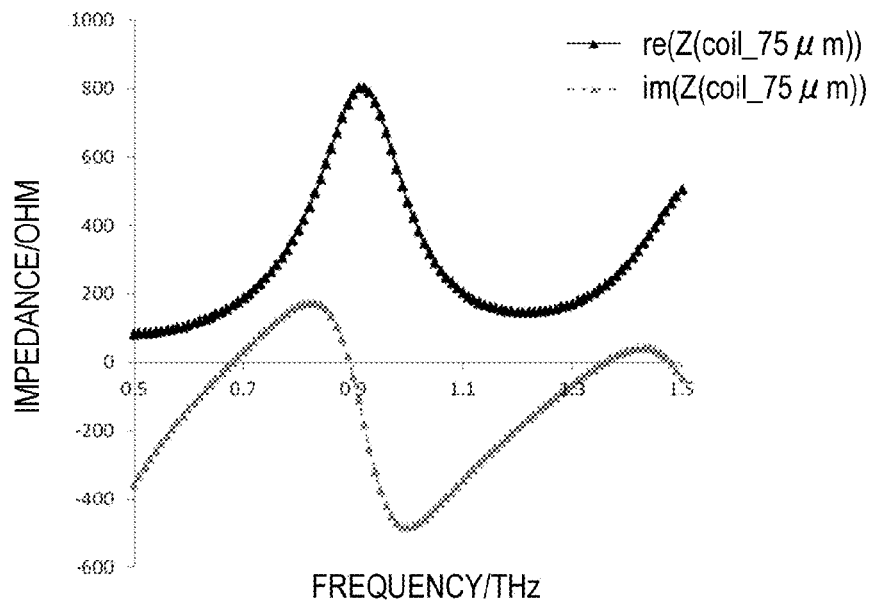
FIG. 4A shows a graph showing an impedance of a loop antenna, 75 μm in radius, around its second antiresonant frequency.
Figure 4B:
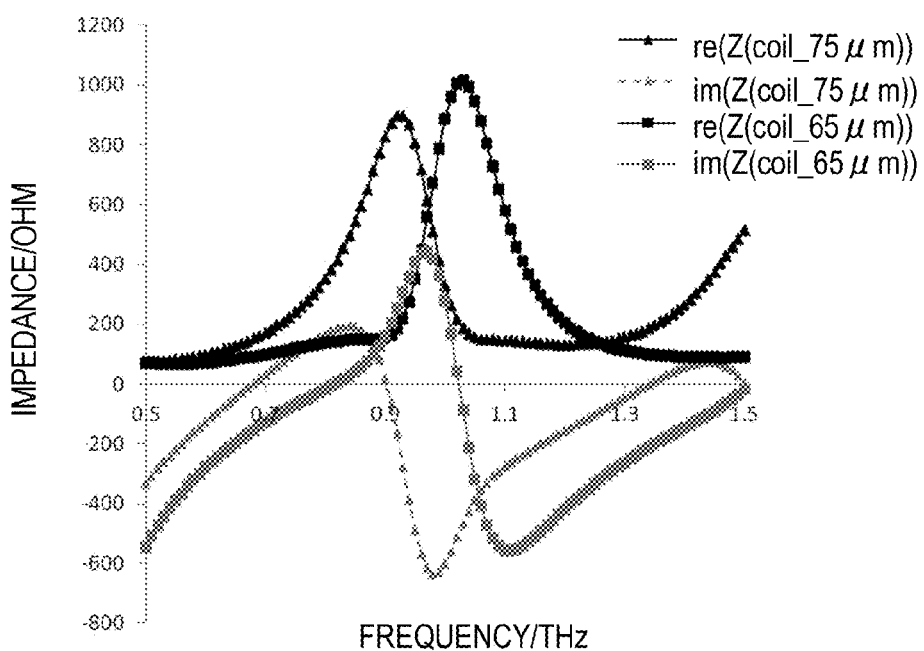
FIG. 4B shows a graph showing an impedance of a sensor of a dual-loop antenna illustrated in FIG. 3A.
Figure 5A:
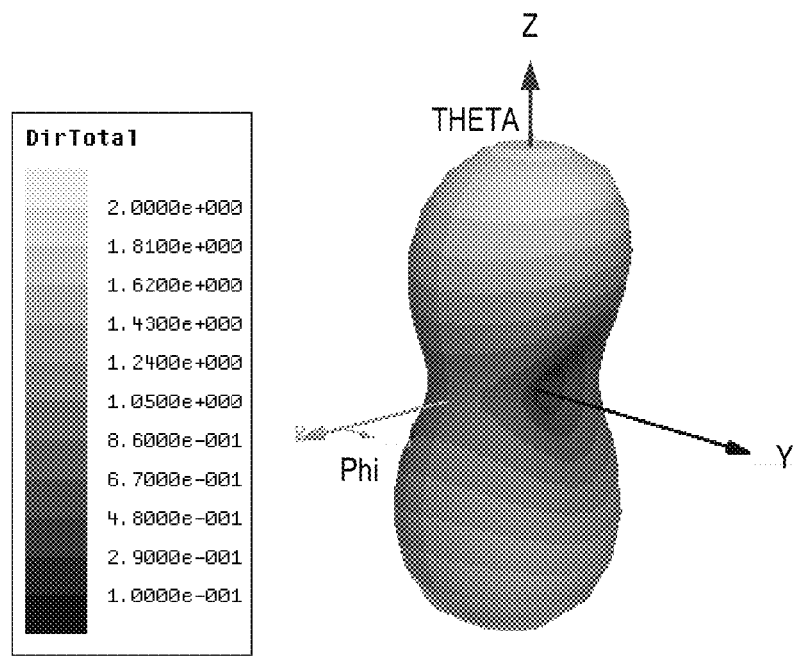
FIG. 5A shows a view illustrating a radiation pattern of a loop antenna having 65 μm in radius illustrated in FIG. 3A.
Figure 5B:
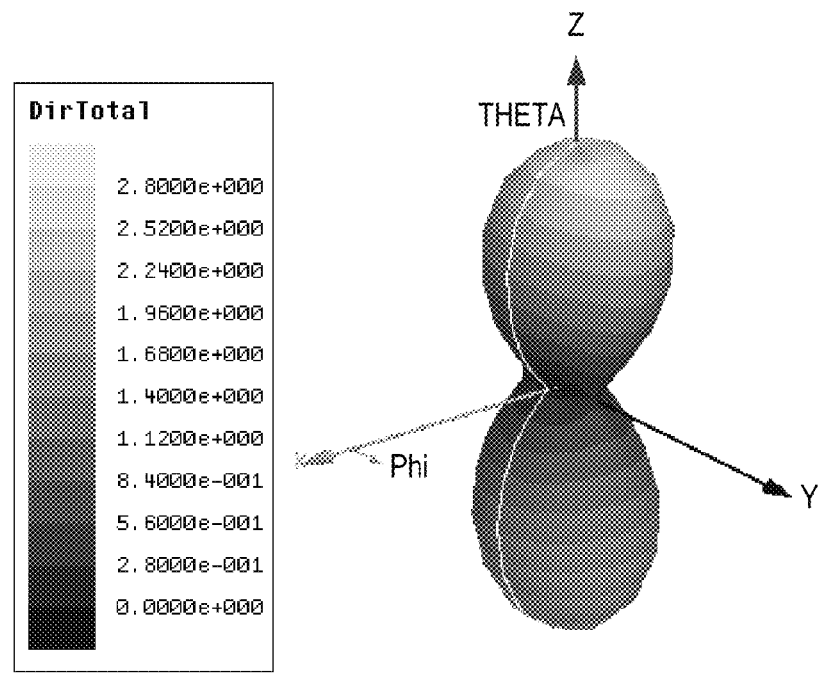
FIG. 5B shows a view illustrating a radiation pattern of the loop antenna having 75 μm in radius illustrated in FIG. 3A.

In this paragraph, simulations results for a two loops sensor obtained with the commercial finite element software HFSS are presented. FIG. 3A shows a system of two loops each one connected to a source and the smallest one included into the largest one. The radius of the smallest one is set to 65 μm and the radius of the largest one is set to 75 μm. FIG. 3B shows the impedance of the smallest loop in case it is alone in vacuum connected to a source. Similarly, FIG. 4A shows the impedance of the largest loop in case it is alone in vacuum and connected to a source. The large peak of the real part of the impedance corresponds to the second antiresonance. FIG. 4B shows the impedance for the system of two loops as shown in FIG. 3A. Despite some small variations, the impedances of the two antennas are not much disturbed by the presence of the other antenna. FIG. 5A and FIG. 5B show the radiation patterns of the smallest and largest antennas, respectively. Compared to the radiation pattern of the single loop antenna shown in FIG. 2A, the radiation pattern of the largest loop is not modified. On the other hand, the radiation pattern of the smallest loop is quite modified; however, most of the radiation is still in the direction perpendicular to the plane of the loop. These simulations demonstrate that this invention provides a sensor in a small footprint for which the radiation impedance and the radiation pattern of both antennas is preserved.

Figure 6A:
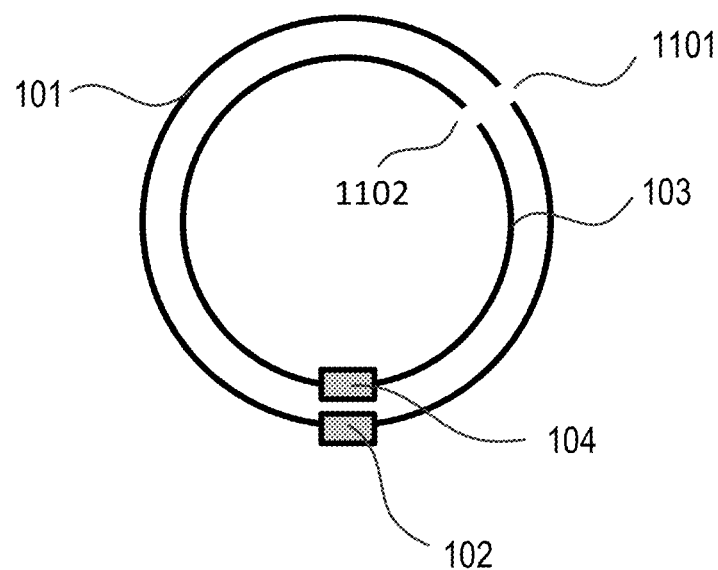
FIG. 6A shows a variation of the radiating elements of the first embodiment, each of which has a cut formed therein.

FIG. 6A shows another variation in which both radiating elements 101 and 103 are loops which include a cut 1101 and 1102, respectively. In other words, the radiating element of the present invention is not limited to the loops and not even limited closed radiating elements. When the radiating element is closed, the voltage rectified by the rectifying element is shunt by the radiating element for a DC current. As a result, all the information originating from the sensor is lost. On the other hand, when the radiating element is open, the voltage rectified by the rectifying element is not shunt by the radiating element and can be used as the information originating from the sensor. In addition to the cut, a resistor, an inductor, a capacitor, or the like may be inserted as a signal extracting portion. It is preferable to position the cut at a minimum of the electromagnetic field on the antenna in order not to disturb the distribution of current, and therefore not to disturb the radiation impedance compared to the case when there is no cut. When a circular loop is excited around its second antiresonant frequency, the minimum of the electrical field corresponds to angles of 120° and 240°, with 0° being the position of the rectifying element. However, the optimum position of the cut depends, in general, on the presence of other elements, such a dielectric or metallic elements, near the loop.

Figure 6B:
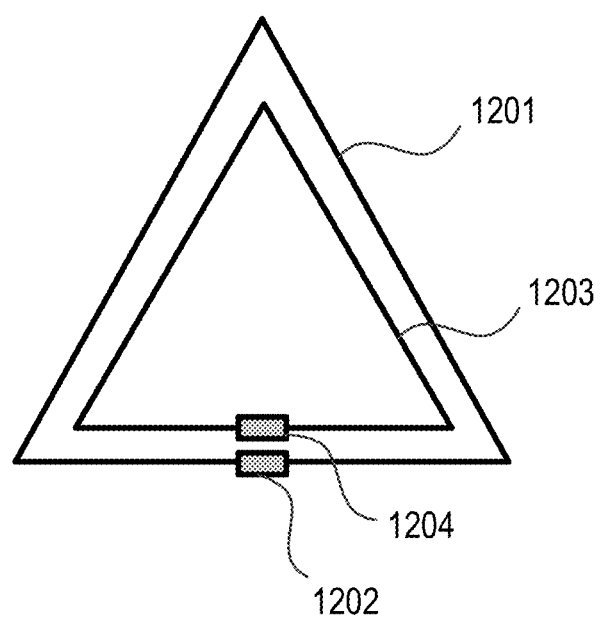
FIG. 6B shows a variation of the radiating elements of the first embodiment, each of which has a triangular shape.

It should be noted that, the loop is not limited to circular loops but is also relevant for loops of any shape. As an example, FIG. 6B shows two triangular loops 1201 and 1203 each connected to a different rectifying element, 1202 and 1204, respectively. The first triangular loop 1201 being larger than the second one 1203 encloses this last. The shape of the loop modifies the radiation impedance of the radiating element, and therefore the conditions of matching with the rectifying element, but does not modify the other characteristics of the invention.

The next variation examines how the two radiating elements can be electrically connected together. When a loop antenna is excited around its second antiresonant frequency, the length of the loop corresponds to 1.5 times the wavelength. As a result, there are three positions in the loop for which the current is maximum. They correspond to a voltage node. When the loop antenna possesses a circular shape, these three nodes positions are the angle 60°, 180°, and 300°, with 0° being the position of the rectifying element. However, the optimum positions of these nodes depend, in general, on the presence of other elements, such a dielectric or metallic elements, near the loop. These three positions correspond to null positions for the electromagnetic field and therefore to a null impedance. Any electrical line connected to these nodes only sees a small current flowing through the line. Therefore, if the two loop antennas are electrically connected at these nodes, the respective radiation impedance of the two loop antennas will not be disturbed compared to the case when the two loop antennas are electrically disconnected.

Figure 7A:
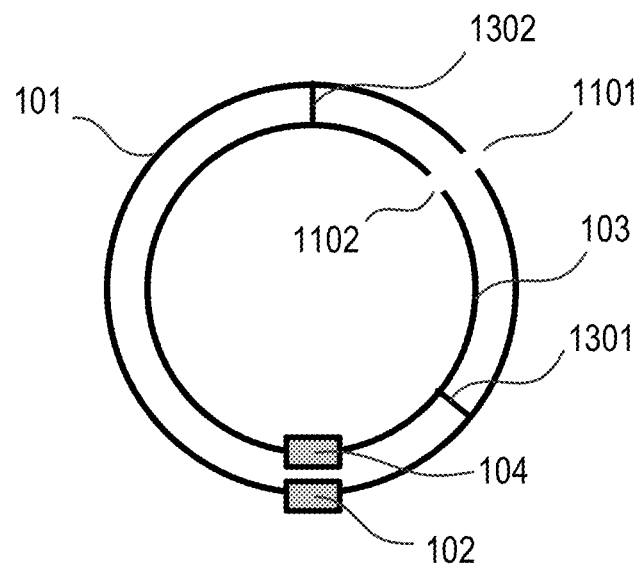
FIG. 7A shows a variation of the first embodiment, in which the radiating elements are connected at two maxima of current.

FIG. 7A shows a variation in which the two circular radiating elements 101 and 103 are connected at the nodes using the connections 1301 and 1302. The main advantage of this variation is that the rectified current originating from the two rectifying elements, in case the antenna is connected to a circuit with a high impedance, will be able to flow in the same electrical circuit, which reduces the number of connections and therefore simplify the design.

Figure 7B:
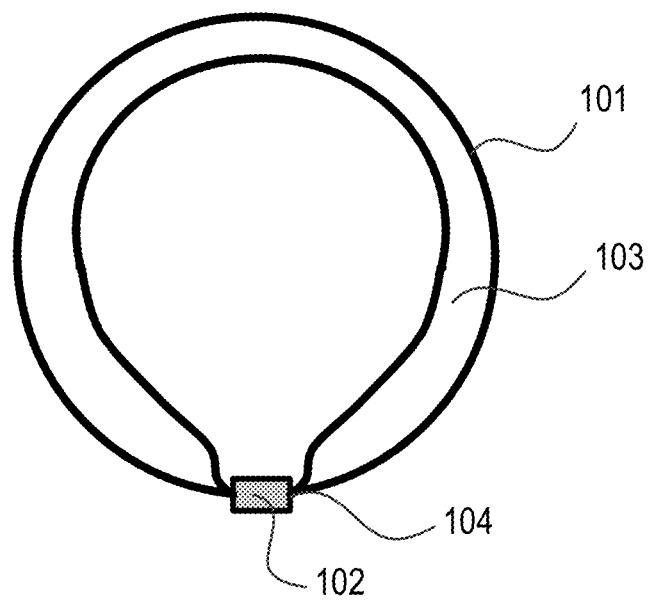
FIG. 7B shows a variation of the first embodiment, in which the two rectifying elements are stacked.

FIG. 7B shows another variation in which the second rectifying element 104 is not placed inside the first radiating element 101, but is stacked on the first rectifying element 102. This has a benefit of reducing the overall size of the sensor. Moreover, this variation can result in a simpler fabrication process. On the other hand, because the two radiating elements 101 and 103 do not cross each other, they do not disturb each other, and therefore their radiation impedance. As a result the efficiency of both antennas is not modified compared to the case when only one radiating element is present.

Figure 8A:
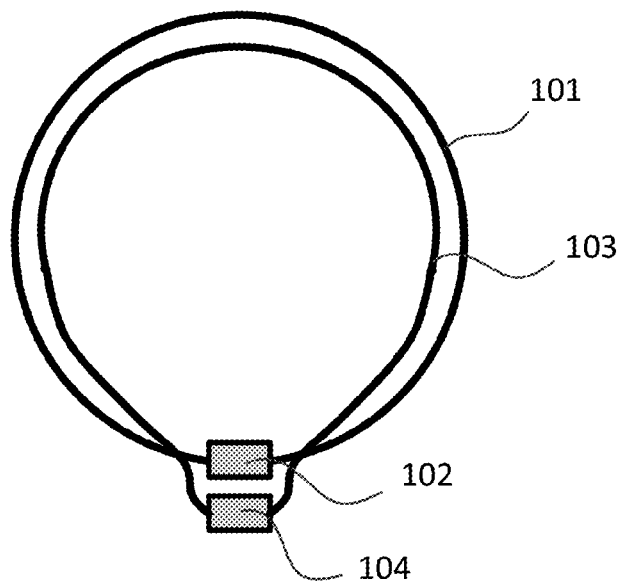
FIG. 8A shows a variation of the first embodiment in which the rectifying element of the second antenna shows placed outside the first radiating element and the second radiating element crosses the first one at the minima of current.

FIG. 8A shows another variation in which the second rectifying 104 element is placed outside the first radiating element 101. This variation can be interesting in order to design the transmission lines connecting to the radiating elements. In this variation, the second radiating element 103 needs to cross the first radiating element 101. Obviously, this is done without any electrical contact between the two radiating elements in order not to disturb their radiating impedance. Nevertheless, the proximity of the two radiating elements will result, in general, in the influence of one radiating element on the current passing through the other one, and therefore on a modification of the radiating impedance. In order to minimize the influence of the radiations from one radiating element on the current of the other one, it is of interest that the second radiating element crosses the first one at a position where its current, and therefore its radiation, is minimum.

Figure 8B:
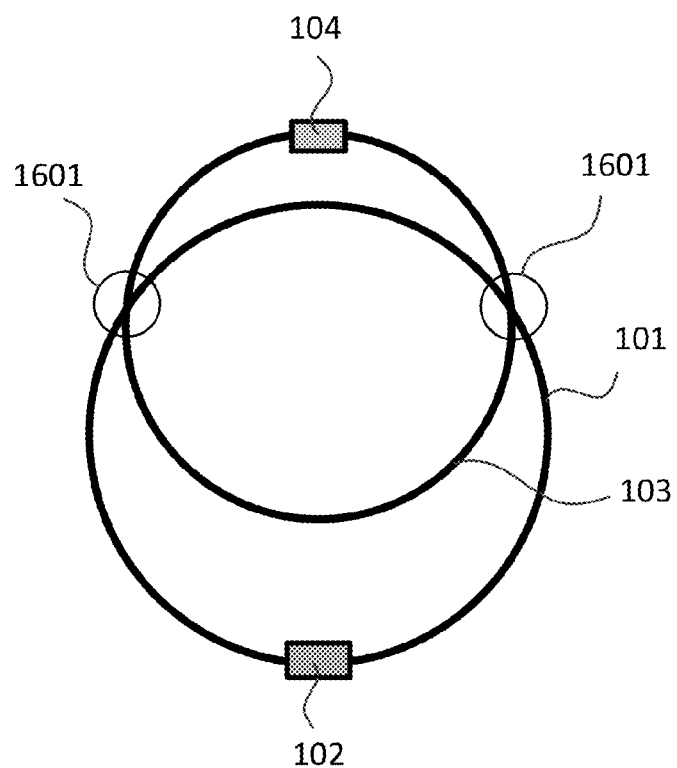
FIG. 8B shows a variation of the first embodiment in which the first radiating element and the second radiating element spatially cross each other at a point having the maximum current, and the rectifier of the second antenna shows arranged outside the first radiating element.

This situation is illustrated in FIG. 8B with two circular loop radiating elements 101 and 103. In this case, the minima of current 1601 are localized at the angle 120°, and 240°, with 0° being the position of the rectifying element. It should be noted that the optimum position of the crossing depends, in general, on the presence of other elements, such a dielectric or metallic elements, near the loop. According to the variation described above, the second radiating element crosses the first radiating element at these positions in order to minimize the influence of the first radiating element on its radiation impedance.

Figure 9A:
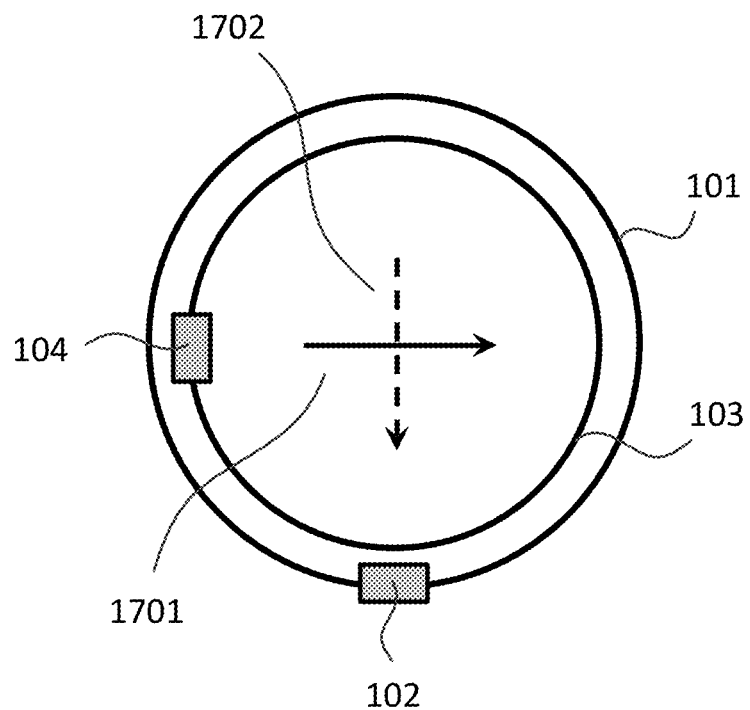
FIG. 9A shows a variation of the first embodiment in which the polarization of the antennas are not aligned.

In the next variation, we wish to show how it is possible to control the polarization of the two antennas formed by two rectifying elements and two radiating elements. It can be of interest that the two sensors performing in the two different frequency bands be sensitive to different polarizations. FIG. 9A shows a variation of the first embodiment in which a first loop radiating element 101 is connected to a first rectifying element 102. When this antenna is used around its second antiresonant frequency, its polarization is linear and is in the direction shown by the solid arrow 1701 in FIG. 9A. A second loop radiating element 103 connected to a second rectifying element 104 placed inside the first loop radiating element 101 will be sensitive to another frequency band when excited around its second antiresonant frequency which corresponds to its length. The polarization 1702 of this second antenna is also linear. By rotating the second antenna with respect to the first one, a sensor sensitive to two different frequencies and two different linear polarizations is possible within a small footprint. The frequency band to which the antennas are sensitive is defined by the length of the loop radiating elements. The relative polarization to which the antennas are sensitive is defined by the relative angle at which they are aligned.

Figure 9B:
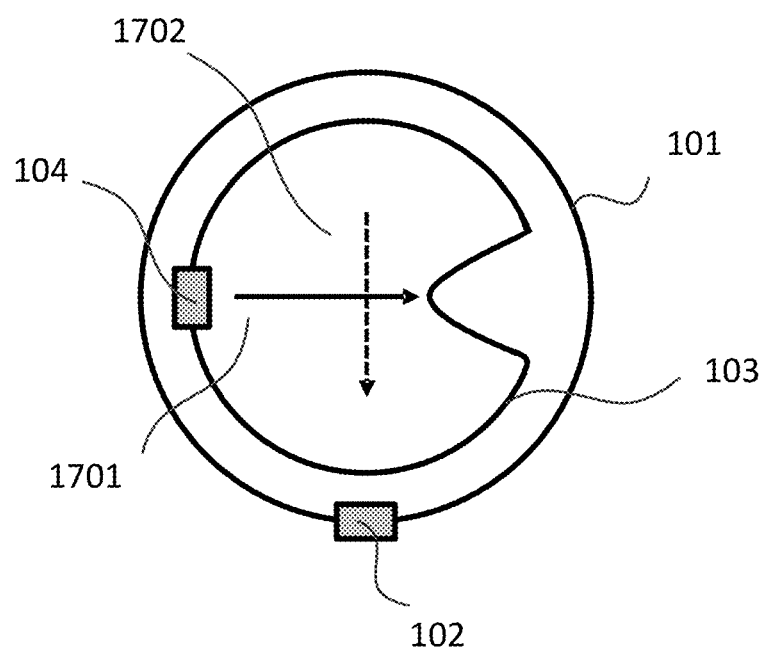
FIG. 9B shows a variation of the first embodiment in which the polarization of the antennas are not aligned, and in which the antiresonant frequency of the inner radiating element shows adjusted by adjusting its length without modifying its surface area.

FIG. 9B shows a variation in which the length of the second loop radiating element 103 has been set independently from its surface area. Because the surface area of the second radiating element is smaller than that of the first radiating element, it can be placed inside this one. On the other hand, its length, and therefore its working frequency band, can be set independently from its surface area. Moreover, its polarization, depending on its angle with respect to the first radiating element, can be set independently furthermore. As a conclusion, the surface area, working frequency band, and polarization can be set independently, resulting in a sensor working in two frequency bands but in a small package.

Figure 10:
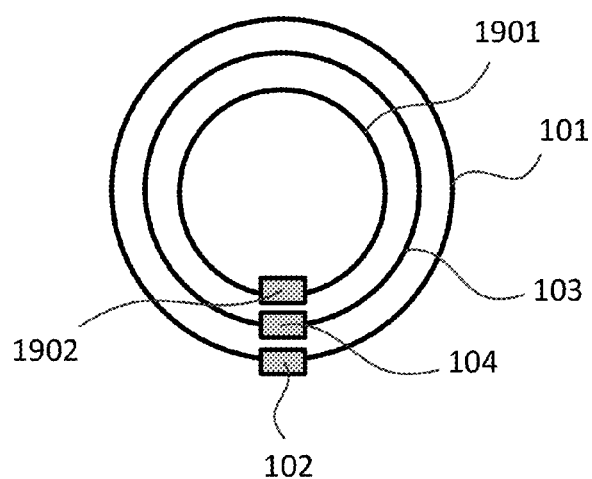
FIG. 10 shows a variation of the first embodiment in which a third antenna shows provided to the sensor.

So far, this embodiment has been limited to two coils, and therefore to two frequency bands which can be sensed by the sensor. FIG. 10 shows this embodiment can be extended to a third frequency band by adding a third antenna inside the radiating element of the second antenna. This third antenna also consists of a rectifying element 1902 and a radiating element 1901 and the surface area of the radiating element is smaller than that of the second radiating element. Of course, we can consider a fourth antenna inserted inside the third one in the same manner. This process can then be continued iteratively.

(Second Embodiment)

The second embodiment deals with the challenge of measuring two frequencies and two polarizations in a small footprint, especially if the working frequency band and surface area of the antenna cannot be set independently as explicated in the first embodiment.

Figure 11:
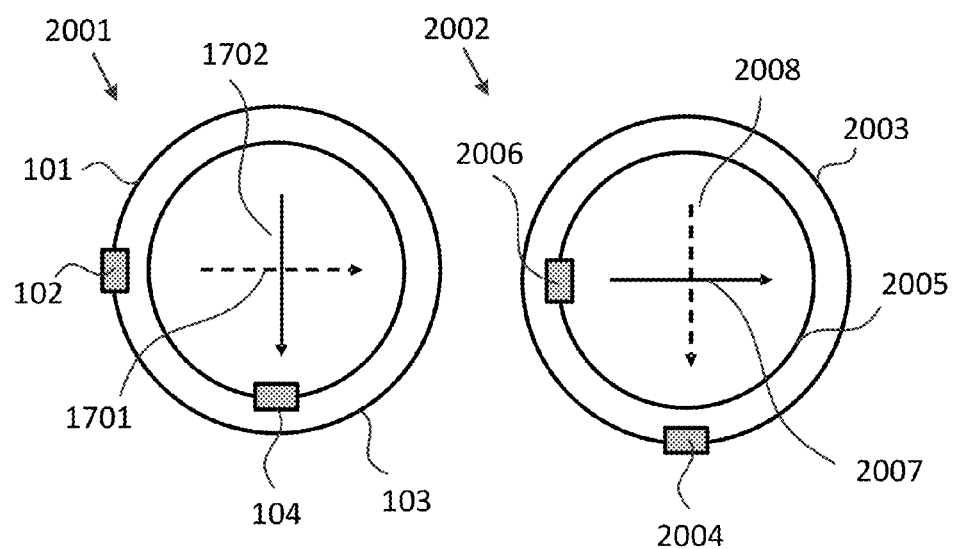
FIG. 11 shows a variation of a second embodiment of the present invention.

In order to fulfill this challenge, two pixels are used. FIG. 11 shows an example of this embodiment in which circular loops are used as the radiating elements. However, the embodiment is not limited to this particular type or shape of radiating elements. In the first pixel 2001, two radiating elements 101 and 103 are connected to two rectifying elements 102 and 104, respectively. They form two antennas. The antenna with the smallest surface area is included inside the larger one, in order to reduce the footprint of the whole sensor. Moreover, the two antennas are linearly polarized with the polarizations 1701 and 1702. By design, the polarizations of the two antennas are not aligned, which is achieved by rotating the two antennas with respect to each other.

The second pixel 2002 is similar to the first one in the sense that it also contains two antennas each one consisting of a radiating element (2003 and 2005) connected to a rectifying element (2004 and 2006), the antenna with the smallest surface area being included in the one with the largest surface area. Moreover, the polarization 2008 of the antenna with the small surface area is the same as the polarization 1702 of the large antenna of the first pixel. Similarly, the polarization 2007 of the antenna with the large surface area is the same as the polarization 1701 of the small antenna in the first pixel. As a result, for each working frequency band, the same two polarizations can be sensed. Also, for each polarization, the same two frequency band can be sensed. Finally, two frequency bands and two polarizations can be sensed within a small footprint.

(Third Embodiment)

The previous embodiments have dealt with sensors which were surrounded by vacuum or by some other homogeneous environment. However, it is of interest to expand this invention in cases where the sensor is integrated with semiconductor devices. By doing so, the sensor can be easily and cheaply mass-fabricated using VLSI fabrication technologies. Moreover, these technologies allow to easily integrated the sensor with various devices fabricated using semiconductors. These devices include transistors, switches, and amplifiers among others.

Figure 12A:
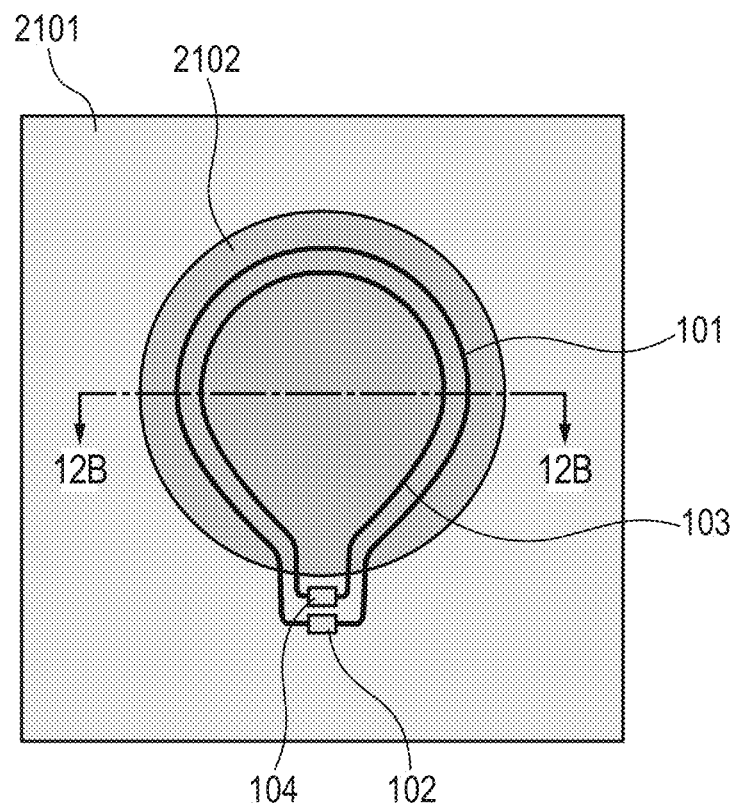
FIG. 12A shows a variation of a third embodiment of the present invention.
Figure 12B:
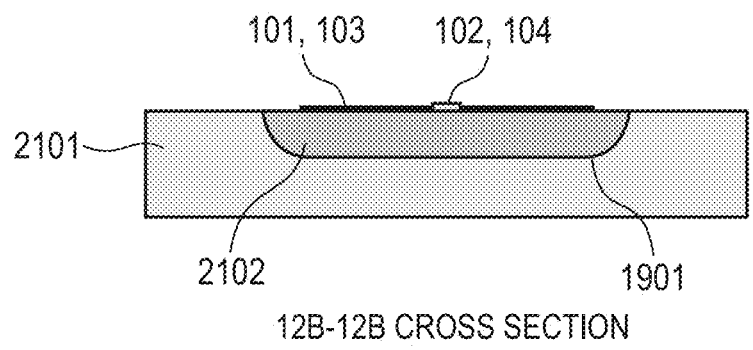
FIG. 12B shows a variation of a third embodiment of the present invention.

FIGS. 12A and 12B show a variation of this third embodiment. A semiconductor substrate 2101 is provided. As in the first embodiment, two loop radiating elements 101 and 103 connected to two rectifying elements 102 and 104, integrated into the substrate 2101, respectively, defines two antennas. The antenna with the smallest surface area is placed inside the largest antenna in order to reduce the overall footprint of the sensor comprising the two antennas. The sensor is integrated on a semiconductor substrate in the following manner. In order to prevent the radiation emitted by the radiating elements to propagate inside the substrate, a recess 1901, which wall is covered with a metallic coating, is provided at the surface of the substrate and the radiating elements are placed above the recess. In order to facilitate the fabrication process or to prevent the radiating element to collapse inside the recess, the recess can be filled with a solid material. The two antennas are electrically connected to an electronic circuit not shown in the figure in order to achieve the sensor using transmission lines on the substrates or via propagating through the depth of the wafer. The signals produced by the antennas can be processed in multiple ways by the electronic circuit. Especially, they can be added or coded in frequency and then transmitted to others circuits integrated in the substrate.

Figure 13:
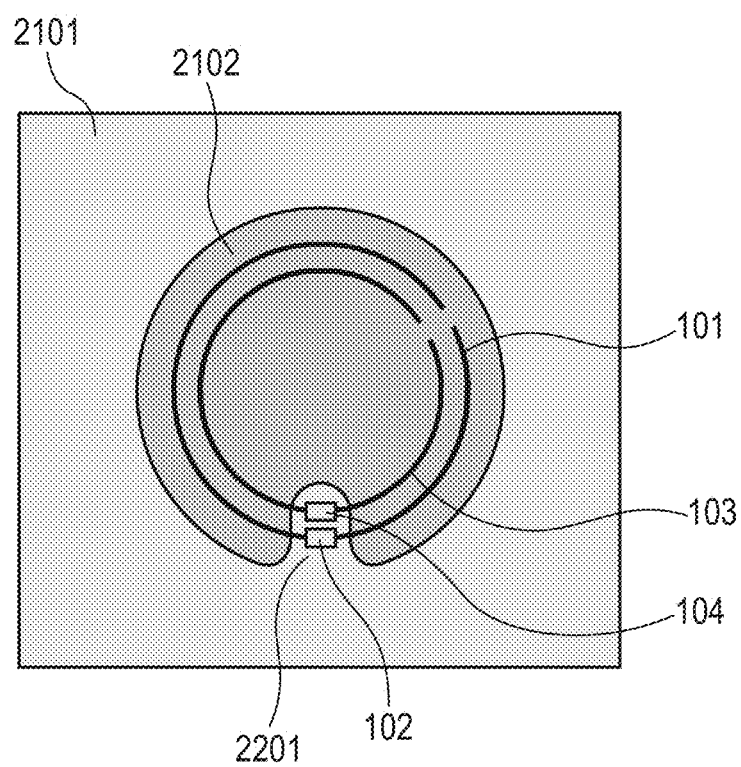
FIG. 13 shows a variation of the third embodiment of the present invention with a support structure for the electric elements and protruding unto the recess.

FIG. 13 shows a variation of this embodiment in which the rectifying elements 102 and 104 are integrated into a support structure 2201 which protrudes into the recess. If the two rectifying elements are close to each other, they can be accommodated on a single support structure. Otherwise two support structure can be provided. This is particularly relevant if the polarizations of the two antennas are not aligned. However, in this case, the support structure corresponding to the inner antenna might disturb the electromagnetic field radiated by the outer antenna and therefore modify its radiation impedance. In this case, it is interesting that the support structure of the inner antenna crosses the radiating element of the outer antenna at a position where its current is minimum.

Figure 14A:
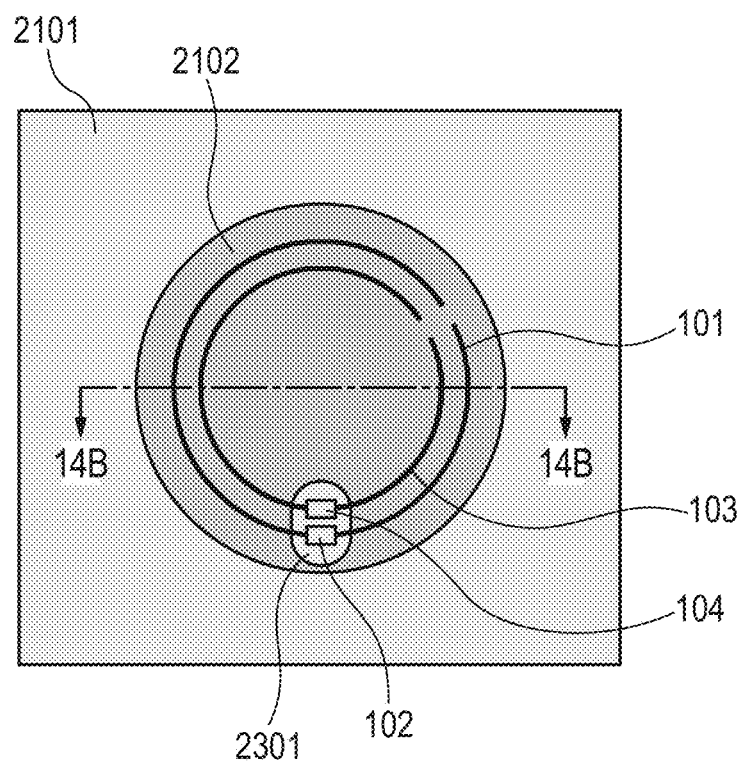
FIG. 14A shows a variation of the third embodiment of the present invention with a pillar.
Figure 14B:
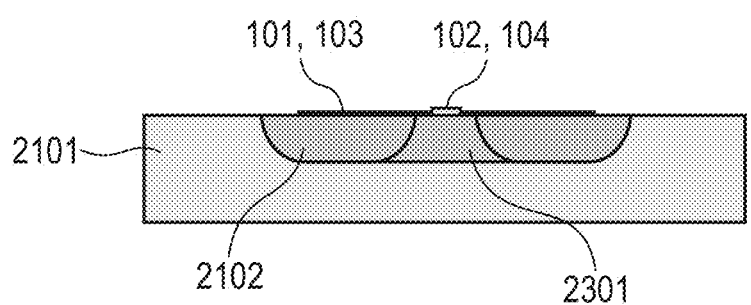
FIG. 14B shows a variation of the third embodiment of the present invention with a pillar.

FIGS. 14A and 14B show a variation of this embodiment in which the rectifying elements 102 and 104 are integrated into a pillar connected to the bottom of the recess. The pillar is a part of the semiconductor substrate. If the two rectifying elements are close to each other, they can be accommodated into a single pillar. Otherwise, two pillars can be provided. If only one pillar is provided, then interactions might arise from electromagnetic waves propagating inside the pillar and originating, for example, from the portion of the radiating elements resting on the pillar. Having a pillar for each rectifying element will reduce these interactions and therefore increase the signal-to-noise ratio of the sensor. The same effect is obtained if the rectifying element of the outer antenna is provided on a support portion and the rectifying element of the inner antenna is provided on a pillar.

This paragraph presents a detailed example of this embodiment. A silicon substrate is provided. Using conventional VLSI technologies, two Schottky barrier diodes are fabricated in the silicon substrate and serve as the rectifying elements. Silicon Schottky barrier diodes operating in the terahertz range have been reported in the past. The recess is etched in the silicon substrate using conventional etching techniques such as $SF_6$ plasma etching for example. The recess is then coated by a metal film using metal evaporation techniques and photolithography based patterning techniques. The recess is then refilled with a dielectric material, such as benzocyclobutene (BCB) which possesses a low refractive index and a good stability. On the refilled recess, the two radiating elements are integrated using metal deposition and patterning.

Figure 15A:
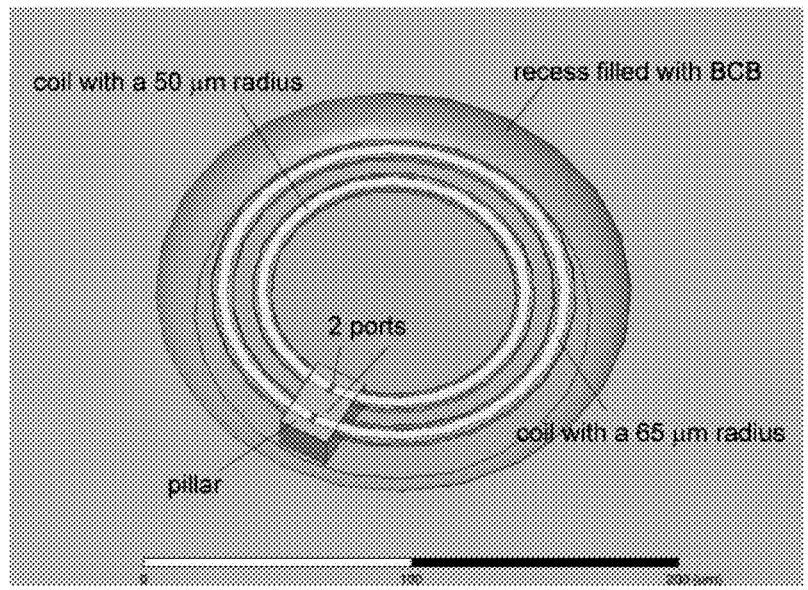
FIG. 15A shows a model used for the simulations corresponding to the third embodiment.
Figure 15B:
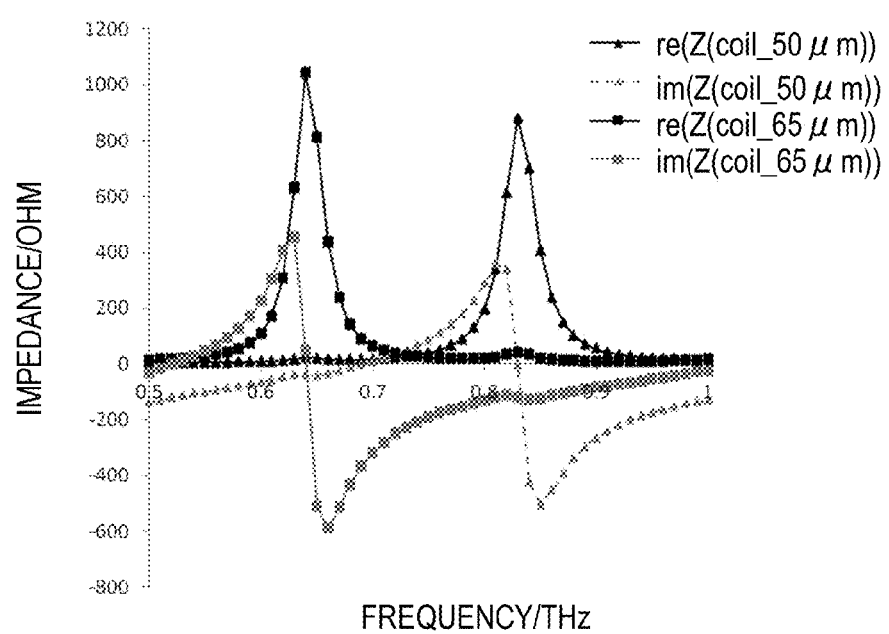
FIG. 15B shows the impedance as calculated by the simulations which corresponds to FIG. 15A.
Figure 16A:
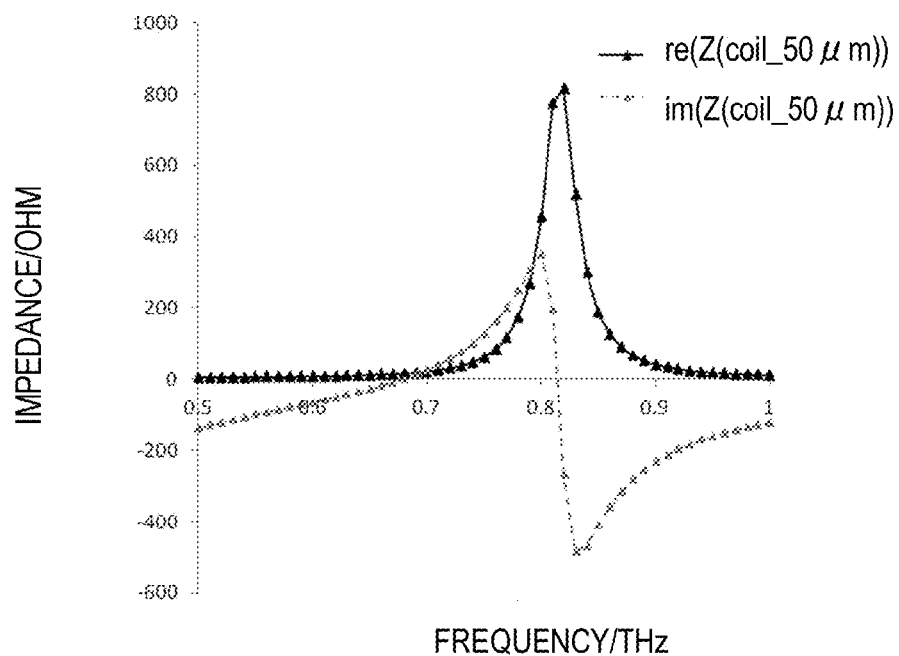
FIG. 16A shows the impedance as calculated by the simulations which corresponds to FIG. 15A when only the antenna with a radius 50 μm is present.
Figure 16B:
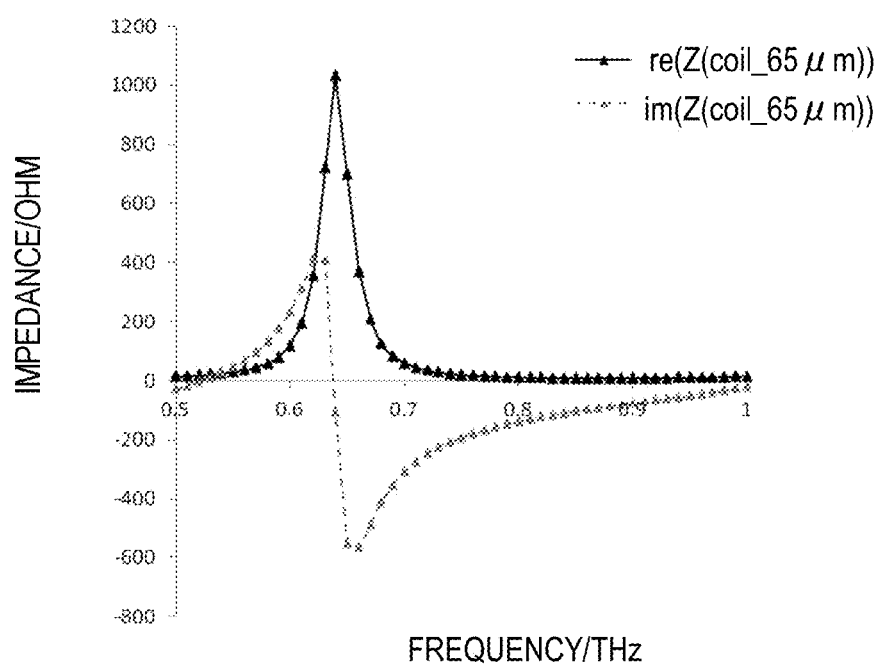
FIG. 16B shows the impedance as calculated by the simulations which corresponds to FIG. 15A when only the antenna with a radius 65 μm is present.

This paragraph presents simulation results obtained by the commercial finite element software HFSS (4). A recess with diameter 90 μm and depth 15 μm is provided in a silicon wafer. The recess is filled with BCB. A pillar, 30 μm in length and 20 μm in width, supports two ports. Two coils, with radius of 50 μm and 65 μm, are connected to the two ports and rests over the recess on the BCB. FIG. 15A shows a drawing of the device used for the simulations. The cuts in the coils have been omitted in order to simplify the simulations. FIG. 15B shows the radiation impedance of the two coils as calculated by HFSS. Moreover, FIG. 16A shows the radiation impedance of the 50 μm radius coil for a device in which only this coil is present. The large peak for the real part around 0.82 THz corresponds to the second antiresonant frequency. Finally, FIG. 16B shows the radiation impedance of the 65 μm radius coil for a device in which only this coil is present. The large peak for the real part around 0.64 THz corresponds to the second antiresonant frequency. In FIG. 15B, we can see that the impedance of each coil is almost not disturbed by the presence of the other coil. This is because the radiation of electromagnetic waves in the plane of the coil, where the other coil is placed, is much smaller than its radiation in the direction perpendicular to its plane. These simulation results demonstrate the effectiveness of this invention.

(Fourth Embodiment)

Arrays of sensors can be used as an image sensor. This technology is well known in the optical field in which CCD (charge-coupled device), CMOS (complementary metal-oxide-semiconductor) sensors, and, in the past, photographic films have been used in cameras in order to record images.

Images sensors have also been developed in other frequency ranges, such as millimeters waves and terahertz.

Figure 17A:
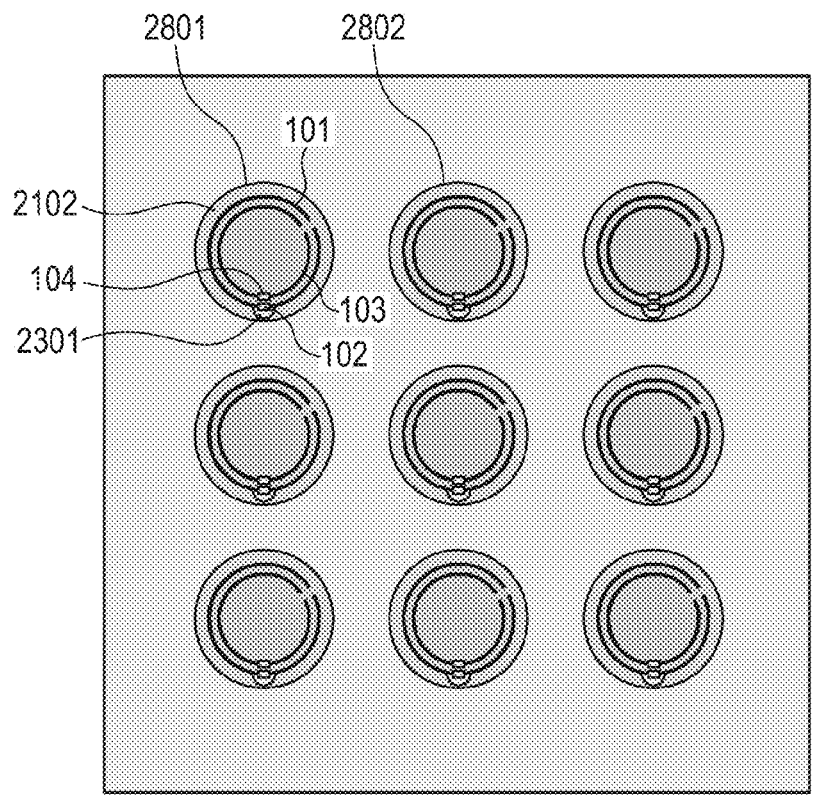
FIG. 17A shows a variation a fourth embodiment of the present invention.

Although this invention is interesting when designing a single sensor, it is particularly interesting when designing an array of sensors, and therefore applied to the design of image sensors. Indeed, one of the merits of this invention is to provide a sensor with a small footprint when compared to previous designs. In the case of an array of sensors, the reduction in footprint is as much important as the number of sensors is large. FIG. 17A shows a realization of this invention. An array of sensors is provided in a semiconductor substrate. FIG. 17A shows an array of nine of such sensors. For example, the semiconductor substrate is a silicon substrate, which allows for compatibility with CMOS technology. Each sensor, 2801, 2802 and so on, consists in a recess etched in the silicon substrate using for example $SF_6$ plasma etching, a pillar, integrating two rectifying elements, for example two Schottky barrier diodes operating in the terahertz range, and two radiating element which are metal patterns connected each to a rectifying element and fabricated using metal deposition and patterning. In order to simplify the fabrication process, the recess can be filled with a dielectric material, for example BCB which has a good stability and a low dielectric constant. Moreover, in order to prevent the radiations emitted by the antennas to penetrate the silicon substrate, the recess is coated by a metallic film.

In FIG. 17A, the two radiating elements are circular loops operating around their second antiresonant mode because this mode presents a radiation pattern mostly in the direction perpendicular to the plane of the coil. They present a cut in order to prevent the rectified part of the signal to be shunt by the radiating element itself. The smallest radiating element is placed inside the largest one in order to reduce the foot print of the whole sensor. The other sensors have basically the same properties has the one described above. However, they may differ in size in order to be sensitive to other frequencies. Moreover, FIG. 17A shows a cubic arrangement of the sensors, but other arrangements are possible, as for example the hexagonal arrangement which is known to be more compact.

(Fifth Embodiment)

It is well known that an antenna can be used for, not only, a device for performing detection of electromagnetic waves, but also, a device for performing emission of electromagnetic waves. In both cases, the impedance and the radiation pattern of the antenna are the same. The difference lies in the electronic device which is connected to the radiating element. In the case of an emitter, the electronic device is, for example, an oscillator which generates electric energy. In the case of a receiver, the electronic device is, for example, a rectifier which converts the energy received by the radiating element in another form. For example, in the case of the rectifier, the frequency of the rectifier is changed.

Figure 17B:
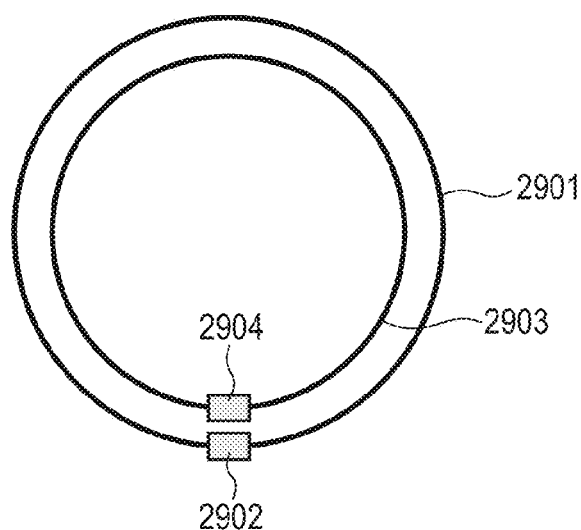
FIG. 17B shows a variation a fifth embodiment of the present invention.

In its fifth embodiment, the present invention provides an emitter, operating in two frequency bands and characterized by a small footprint. FIG. 17B shows a variation of the fifth embodiment. A first radiating element 2901 is electrically connected to a first oscillator 2902, forming a first antenna. A second radiating element 2903 is electrically connected to a second oscillator 2904, forming a second antenna. The two radiating elements are electrically disconnected in order not to disturb the impedance of the radiating elements and therefore the impedance matching with the oscillators. Moreover, the second antenna is such that its surface area is smaller than that of the first one. In order to reduce the overall footprint of the emitter constituted by the two antennas, the second antenna is placed inside the first radiating element.

Following the results presented in the first embodiment for a sensor using similar radiating elements and according to the equivalence between emitters and sensors using antennas, it can be understood that the emitter described above operates in two frequency bands, possesses a small footprint, and preserves the impedance matching for each antenna. Furthermore, because of the equivalence between emitters and sensors using antennas, all the variations presented in the previous embodiments can be adapted to the case of an emitter based on the present embodiment.

As set forth hereinabove, according to the embodiments of the present invention, because the sensor includes a plurality of antennas which are sensitive to the different frequency bands, the sensor which has the sensitivity to the different frequency bands, and so on can be realized. In addition, because one radiating element surrounds in its inside at least a part of the other radiating element, the size can be reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-235033, filed Nov. 13, 2013, which is hereby incorporated by reference herein in its entirety.

What is claimed is:

1. A sensor for detecting terahertz waves, comprising:
a semiconductor substrate;
a firing wiring loop;
a first rectifier electrically connected to the first wiring loop;
a second wiring loop; and
a second rectifier electrically connected to the second wiring loop, wherein
the first wiring loop surrounds at least a part of the second wiring loop,
wherein the first wiring loop, the first rectifier, the second wiring loop and the second rectifier are arranged on same surface side of the semiconductor substrate, and
wherein the first wiring loop and the second wiring loop have different shapes from each other, and are sensitive to terahertz waves with different polarization directions from each other.

2. The device according to claim 1, wherein a recess is provided at the surface of the substrate,
wherein the first wiring loop is arranged above the recess, and
wherein the second wiring loop is arranged above the recess.

3. A device according to claim 2, wherein the recess is filled with a material.

4. A device according to claim 2, further comprising a support portion that protrudes to the recess and is configured to support at least one of the first electronic element or the second electronic element.

5. A device according to claim 4, wherein the support portion for the second electronic element crosses the first antenna in a position of the first radiating element at which a current is minimum.

6. The sensor according to claim 2, wherein the recess is covered with the metal coating.

7. The device according to claim 1, wherein-the second rectifier is placed inside the first wiring loop.

8. The sensor according to claim 1, wherein
the first rectifier is a first Schottky barrier diode,
the second rectifier is a second Schottky barrier diode,
the first wiring loop has a first end portion and a second end portion, the first Schottky barrier diode is positioned between the first end portion and the second end portion, and
the second wiring loop has a third end portion and a fourth end portion, and the second Schottky barrier diode is positioned between the third end portion and a fourth end portion.

9. The sensor according to claim 1, further comprising:
a metal coating arranged between a surface opposite the surface of the substrate and the first and second wiring loops.

10. The device according to claim 1, wherein a first plane on which the first wiring loop is placed and a second plane on which the second wiring loop is placed are parallel to each other, and
wherein the first plane and the second plane are separated by a distance of 1/10 of less of a wavelength corresponding to a minimum working frequency.

11. The device according to claim 1, wherein the first wiring loop is sensitive to a first frequency band of interest,
wherein the second wiring loop is sensitive to a second frequency band of interest, and
wherein the first frequency and the second frequency are same to each other.

12. The device according to claim 1, wherein the first wiring loop and the second wiring loop are arranged on the same plane.

13. The device according to claim 1, wherein the first wiring loop and the second wiring loop are configured to receive linearly polarized light beams that are different in polarization direction from each other.

14. A emitter for emitting terahertz waves, comprising:
a semiconductor substrate;
a first wiring loop;
a first oscillator electrically connected to the first wiring loop;
a second wiring loop; and
a second oscillator electrically connected to the second wiring loop; wherein
the first wiring loop surrounds at least a part of the second wiring loop,
wherein the first wiring loop, the first oscillator, the second wiring loop and the second oscillator are arranged on same side surface of the semiconductor substrate, and
wherein the first wiring loop and the second wiring loop have different shapes from each other, and are sensitive to terahertz waves with different polarization directions from each other.

15. The emitter according to claim 14, wherein
the first wiring loop has a first end portion and a second end portion, the first oscillator is positioned between the first end portion and the second end portion,
the second wiring loop have a third end portion and a fourth end portion, and the second oscillator is positioned between the third end portion and fourth and portion.

16. A sensor for detecting terahertz waves, comprising:
a semiconductor substrate;
a first wiring loop;
a first rectifier electrically connected to the first wiring loop;
a second wiring loop; and
a second rectifier electrically connected to the second wiring loop, wherein the first wiring loop surrounds at least a part of the second wiring loop,
wherein the first wiring loop, the first rectifier, the second wiring loop and the second rectifier are arranged on same surface side of the semiconductor substrate, and
wherein the second wiring loop crosses the first wiring loop at a position at which a current is minimum.

17. The sensor according to claim 16, wherein the first wiring loop is different in length from the second wiring loop.

18. The device according to claim 16, wherein the first wiring loop and the second wiring loop are electrically disconnected from each other.

19. An apparatus, comprising a plurality of devices for performing detection of terahertz waves including a first devices and a second devices sensing terahertz waves,
the first devices and the second devices each comprising;
a semiconductor substrate;
a first wiring loop;
a first rectifier electrically connected to the first wiring loop;
a second wiring loop; and
a second rectifier electrically connected to the second wiring loop, wherein
the first wiring loop surrounds at least a part of the second wiring loop,
wherein the first wiring loop, the first rectifier, the second wiring loop and the second rectifier are arranged on same surface side of the semiconductor substrate,
wherein, in the first devices sensing terahertz waves, an antenna that is sensitive to a higher frequency is sensitive to first polarization and an antenna that is sensitive to a lower frequency is sensitive to second polarization, and
wherein, in the second devices sensing terahertz waves, an antenna that is sensitive to the lower frequency is sensitive to the first polarization, and an antenna that is sensitive to the higher frequency is sensitive to the second polarization.

* * * * *